United States Patent [19]
Ohgi et al.

[11] Patent Number: 5,703,224
[45] Date of Patent: Dec. 30, 1997

[54] ANTIVIRAL C-NUCLEOSIDE DERIVATIVES

[75] Inventors: Tadaaki Ohgi, Shiga; Junichi Yano, Nara, both of Japan

[73] Assignee: Nippon Shinyaku Co. Ltd., Japan

[21] Appl. No.: 652,584

[22] PCT Filed: Dec. 9, 1994

[86] PCT No.: PCT/JP94/02059

§ 371 Date: Aug. 26, 1996

§ 102(e) Date: Aug. 26, 1996

[87] PCT Pub. No.: WO95/15964

PCT Pub. Date: Jun. 15, 1995

[30] Foreign Application Priority Data

Dec. 10, 1993 [JP] Japan .................. HEI-5/310622

[51] Int. Cl.$^6$ .................................................. C07H 19/00
[52] U.S. Cl. ............................ 536/29.2; 536/1.11
[58] Field of Search ................... 536/28.1, 29.2, 536/1.11

[56] References Cited

U.S. PATENT DOCUMENTS 5,393,879  2/1995  Wang et al. ............................ 536/29.2

OTHER PUBLICATIONS

Farkas, Collection of Czechoslov. Chem. Commun., 1971, 36, 3043–46.
Montgomery et al., 1-(Adenin-9-yl)-2,5-anhydro-1-deoxy-D-allitol, A Homolog of Adenosine, J. Heterocycl. Chem., 1970, 7, 443–445.
Holy, Collection of Czechoslov. Chem. Commun., 1970, 35, 81–88.
Bobek et al., Collection of Czechoslov. Chem. Commun., 1969, 34, 1684–89.

*Primary Examiner*—John Kight
*Assistant Examiner*—Friedrich N. Burnett
*Attorney, Agent, or Firm*—Graham & James LLP

[57] ABSTRACT

The present invention is composed of a nucleoside derivative of the following general formula [I]:

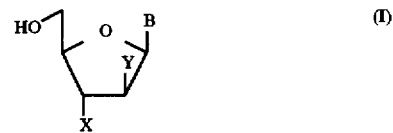

(wherein B represents adenin-9-ylmethyl, guanin-9-ylmethyl, hypoxanthin-9-ylmethyl, thymin-1-ylmethyl, uracil-1-ylmethyl, or cytosin-1-ylmethyl; X and Y may be the same or different and each represents hydrogen or hydroxy, exclusive of the case in which X is hydrogen and Y is hydroxy).

The compound of the present invention is useful as an antiviral agent or an antimalignant-tumoral agent.

2 Claims, No Drawings

ANTIVIRAL C-NUCLEOSIDE DERIVATIVES

This application is a 371 of PCT/JP 94/02059 filed Dec. 12, 1994.

TECHNICAL FIELD

The present invention relates to a novel nucleoside derivative having antiviral or antimalignant-tumoral activities.

BACKGROUND TECHNOLOGY

Being transmitters of genetic information in living matter, nucleic acids play a crucial role in the differentiation and growth of cells. Among natural and unnatural nucleoside derivatives, many derivatives are known to inhibit biosynthesis of nucleic acids and are, therefore, useful as antiviral or antimalignant-tumoral agents. As antiviral agents, for instance, vidarabine (Ara-A: C. R. Acad. Soc. D (Paris), 259, 2725 (1964)), acyclovir (Proc. Natl. Acad. Sci, USA, 74, 5716 (1977)), azidothymidine (Proc. Natl. Acad. Sci, USA, 82, 7096 (1985)), 2',3'-dideoxyinosine (DDI), 2',3'-dideoxycytidine (DDC: WO90/14079), among other nucleosides, are known. As antimalignant-tumoral agents, cytarabine (Ara-C), enocitabine, thioinosine, etc. are known.

However, none of the above-mentioned antiviral agents and antimalignant-tumoral agents are fully satisfactory from the standpoint of effects and adverse actions. It is guessed to be one of the causes for insufficient efficacy that the above-mentioned nucleoside derivatives have the chemical structure in which the nucleic acid base moiety is directly bound to the sugar one and, therefore, they are susceptible to hydrolysis by acid or alkali and the nucleoside derivatives with activity are ready to be metabolized in living body.

Meanwhile, as the compounds resembling the compound of the present invention, there are known several nucleosides having the chemical structure in which a methylene group is inserted between the nucleic acid base moiety and the sugar one. They are generally called homonucleosides. For example, 2,5-anhydro-1-doexy-1-(adenin-9-yl)-D-allitol (1-homoadenosine: Collection Czechoslov. Chem. Commun., 36, 3043 (1971) and J. Heterocycl. Chem., 7, 443 (1970)), 2,5-anhydro-1-deoxy-1-(uracil-1-yl)-D-allitol (1-homouridine: Collection Czechoslov. Chem. Commun., 34, 1684 (1969) and Collection Czechoslov. Chem. Commun., 35, 81 (1970)), 2,5-anhydro-1-deoxy-1-(cytosin-1-yl)-D-allitol (1-homocytidine: Collection Czechoslov. Chem. Commun., 34, 1684 (1969)), 2,5-anhydro-1,3,4-trideoxy-1-(6-mercaptopurin-9-yl)-D-allitol, and 2,5-anhydro-1,3,4-trideoxy-1-(6-methylthiopurin-9-yl)-D-allitol (J. Med. Chem., 15, 571 (1972)) are known. However, useful pharmacologic activities of these compounds are not disclosed at all. Quite recently, a nucleoside containing an oxetanocin ring suggested its possibility as an antiviral and anticancer agent has been reported (Japanese Laid-Open H. 5-271224).

DISCLOSURE OF THE INVENTION

The object of the present invention is to provide, as a medicine, a homonucleoside derivative which is difficult to be subjected to acid and alkali hydrolysis, and is chemically and enzymologically stable by inserting a methylene group between the nucleic acid base moiety and the sugar one of a nucleoside derivative.

The inventors of the present invention have researched in earnest and have found that a compound of the following general formula [I] meet the above-mentioned object and then have completed the present invention.

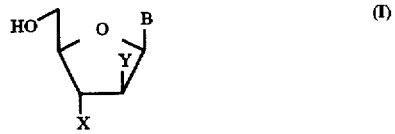

wherein B represents adenin-9-ylmethyl, guanin-9-ylmethyl, hypoxanthin-9-ylmethyl, thymin-1-ylmethyl, uracil-1-ylmethyl, or cytosin-1-ylmethyl; X and Y may be the same or different and each represents hydrogen or hydroxy, with the exception of the case in which X is hydrogen and Y is hydroxy.

The feature of the present invention exists in the very structure of the compound of general formula [I]. The compound of the present invention is a novel compound not heretofore described in the literature.

Moreover, as above-mentioned, owing to its enhanced stability, both chemically and enzymologically, the compound of the invention is difficult to be metabolized in living body, so that its pharmacologic effect is increased in both intensity and duration as compared with the conventional nucleosides.

The compound of the present invention has antiviral and antimalignant-tumoral activities and has good stability and safety in living body and, therefore, is useful as a drug.

The compound of the present invention includes the following specific compounds in addition to the compounds mentioned in working examples for production presented later. These compounds are mentioned as an example to show a part of the compound of the present invention. The compound of the present invention is not limited to these compounds.

2,5-Anhydro-1,3,4-trideoxy-1-(guanin-9-yl) -D-allitol,
2,5-arthydro-1,3,4-trideoxy-1-(uraci-1-1-yl) -D-allitol,
2,5-anhydro-1,3,4-trideoxy-1-(cytosin-1-yl)-D-allitol,
2,5-anhydro-1-deoxy-1-(guanin-9-yl) -D-sorbitol,
2,5-anhydro-1-deoxy-1-(hypoxanthin-9-yl) -D-sorbitol,
2,5-anhydro-1-deoxy-1-(thymin-1-yl)-D-sorbitol,
2,5-anhydro-1,3-dideoxy-1-(guanin-9-yl)-D-allitol,
2,5-anhydro-1,3-dideoxy-1-(hypoxanthin-9-yl) -D-allitol,
2,5-anhydro-1,3-dideoxy-1-(cytosin-1-yl)-D-allitol and
2,5-anhydro-1,3-dideoxy-1-(uracil-1-1-yl)-D-allitol.

The compound of the present invention can be produced, for example, by the following production processes. Such production processes are now explained corresponding to the three classes of compounds according to the kinds of X and Y in general formula [I].

1. Production of dideoxy compounds (X=hydrogen, Y=hydrogen)

The compound [Ia] that is the compound [I] wherein X is hydrogen and Y is hydrogen, can be produced, for example, in accordance with the following react ion schema.

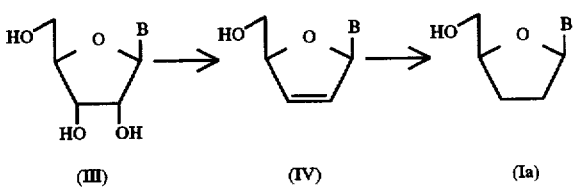

wherein B has the same meaning as defined hereinbefore.

Thus, compound [III] is subjected to dehydroxylation reaction to give compound [IV], which is then reduced to compound [Ia].

The reaction from compound [III] to compound [IV] can be carried out in accordance with the method described in the literature (J. Org. Chem., 54, 4780–4785, 1989), as follows.

In a solvent such as acetonitrile, N,N-dimethylformamide (DMF), or dioxane, compound [III] is reacted with an acyloxyisobutyryl halide such as 2-acetoxyisobutyryl bromide at a temperature between the room temperature and the reflux temperature for 1–2 hours. While the reaction temperature depends on the base of compound [III], a temperature around room temperature is preferred for a purine base and the reflux temperature is preferred for a pyrimidine base.

The resulting reaction product is then dissolved in a suitable solvent and treated with several molar equivalents of Zn (Cu) couple reagent, chromous acetate, zinc/acetic acid, or the like for about 0.5–1 hour. The solvent to be used is preferably a polar solvent such as mixed solvent of methylene chloride and methanol, DMF, acetonitrile, dioxane, etc.

The obtained compound is then treated with a lower alcohol such as methanol, and concentrated aqueous ammonia at room temperature for 5–24 hours, whereby compound [IV] can be produced.

Compound [IV] is subjected to catalytic reduction in a lower alcohol solvent such as methanol or ethanol, in the presence of a hydrogenation catalyst such as palladium chloride, platinum oxide, palladium black or 5% or 10% palladium-on-carbon and at room temperature for 2–10 hours, whereby compound [Ia] can be produced.

2. Production of arabino compounds (X-hydroxy, Y=hydroxy)

(1) In the case of a purine base

The compound [Ib] that is the compound [I] wherein X represents hydroxy and Y represents hydroxy and whose nucleic acid base is a purine base, can be produced, for example, by the reactions illustrated in the following schema.

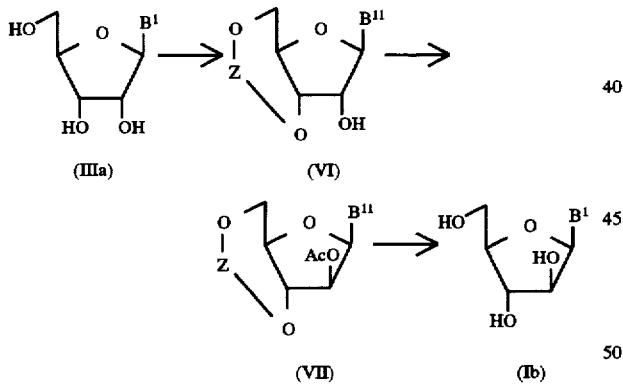

wherein $B^1$ represents adenin-9-ylmethyl or guanin-9-ylmethyl; $B^{11}$ represents $B^1$ wherein protected by a nucleic acid base-protective group which is conventionally used in nucleic acid synthesis (e.g. benzoylated or isobutyrylated $B^1$); Z represents tetraisopropyldisiloxane-1, 3-diyl.

Thus, compound [Ib] can be produced by protecting the nucleic acid base and sugar moieties of compound [IIIa] (compound [III] whose nucleic acid base is a purine base) to give a cyclic compound [VI], then introducing an electron-withdrawing group such as trifluoromethanesulfonyl or methanesulfonyl, into the 2'-position of this compound [VI], and carrying out a nucleophilic substitution reaction to give compound [VII], and deprotecting the compound [VII].

Protection of the amino group of the base moiety of compound [IIIa] can be carried out by the method described in literatures (benzoyl for adenine: J. Am. Chem. Soc., 85, 3821 (1963); isobutyryl for guanine: J. Mol. Biol., 72, 251 (1972)) or any method analogous therewith. Then, for protection of the sugar moiety, the compound is treated with 1–1.2 molar equivalents of 1, 1,3,3-tetraisopropyl-1,3-dichlorodisiloxane at room temperature for 1–4 hours to give compound [VI].

In an aprotic solvent such as methylene chloride, and in the presence of a base such as pyridine, compound [VI] is reacted with trifluoromethanesulfonic anhydride at 0° C. for 0.5–3 hours, whereby the O-trifluoromethanesulfonyl compound can be obtained. This compound is reacted with a nucleophilic reagent such as lithium acetate in a polar solvent such as DMF, dimethyl sulfoxide (DMSO) or hexamethylphosphoramide (HMPA), at 10°–50° C. for 2–24 hours, whereby the steric configuration at the reaction site is inverted to give compound [VII] having the substituent group introduced selectively in β-configuration.

Deprotection of compound [VII] can be carried out by known procedures, for example, by treatment with concentrated aqueous ammonia and, then, with a mineral acid such as hydrochloric acid.

(2) In the case of a pyrimidine base

The compound [Ic] and the compound [Id] that are the compound [I]of the invention wherein X represents hydroxy and Y represents hydroxy and whose nucleic acid base is a pyrimidine base, can be produced, for example, by the reactions illustrated in the following schema.

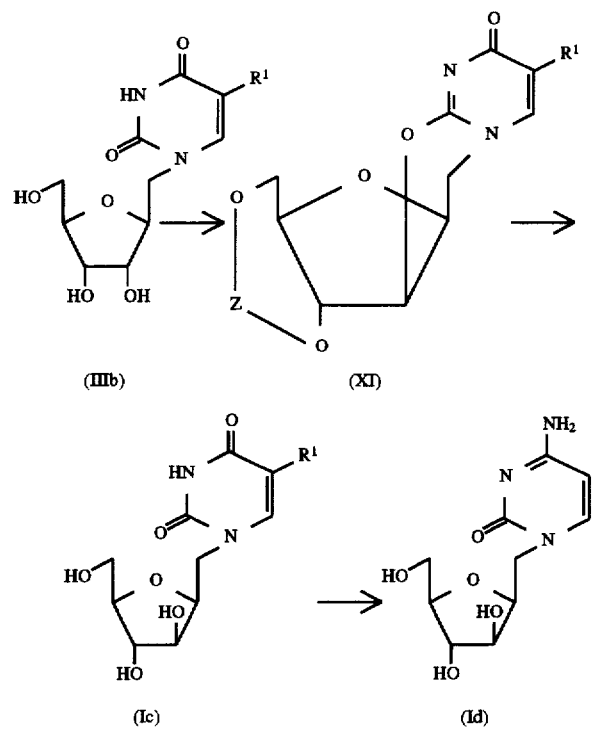

wherein Z has the same meaning as defined hereinbefore; $R^1$ represents hydrogen or methyl.

Thus, compound [Ic] can be produced by protecting the sugar moiety of compound [IIIb], then carrying out a trifluoromethanesulfonylation reaction followed by an intramolecular nucleophilic substitution reaction to give compound [XI], and deprotecting [XI]. Starting with compound [Ic] ($R^1$=hydrogen), compound [Id] can be produced by the per se known method.

Protection of the sugar moiety of compound [IIIb] can be carried out using 1,1,3,3-tetraisopropyl-1,3-dichlorodisiloxane in the same manner as described above. The resulting compound is then reacted with trifluoromethanesulfonic anhydride in an aprotic solvent such as methylene chloride, in the presence of a base such as pyridine, at 0° C. for 0.5–3 hours to give the O-trifluoromethane-sulfonyl compound followed by an intramolecular nucleophilic substitution reaction of this compound at 10°–50° C., preferably at room temperature, whereby compound [XI] can be obtained.

Production of compound [Ic] by deprotection of compound [XI] can be carried out in the same manner as described hereinbefore.

Production of compound [Id] from compound [Ic] ($R^1$= hydrogen) can be carried out by the method described in a literature (Carbohydrate Research, 31, 245, 1973) or any method analogous therewith. Thus, compound [Id] can be obtained by reacting a compound [Ic] ($R^1$=hydrogen) with acetic anhydride and pyridine at room temperature to protect the hydroxyl group with acetyl, then reacting the protected compound with phosphorus pentasulfide to give the thiouracil compound, and treating the thiouracil compound with ammonia.

3. Production of monodeoxy compounds (X=hydroxy, Y=hydrogen)

The compound [Ie]]that is the compound [I] of the invention wherein X is hydroxy and Y is hydrogen and whose nucleic acid base is a purine base, can be produced by the reactions illustrated in the following schema.

Process A

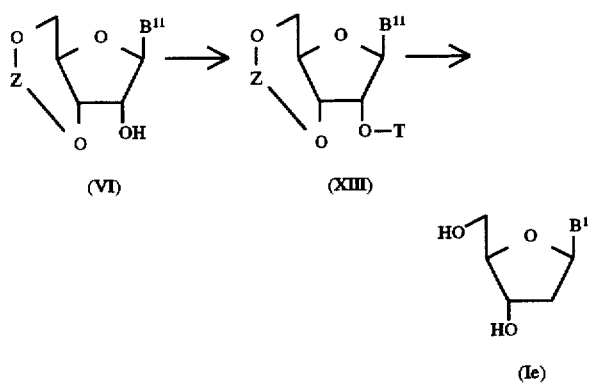

wherein $B^1$, $B^{11}$, and Z have the same meanings as defined hereinbefore. T represents substituted thiocarbonyl such as imidazolylthiocarbonyl, phenoxythiocarbonyl.

Thus, compound [VI] is thiocarbonylated to give compound [XIII] which is reduced and then deprotected, whereby compound [Ie] can be produced.

Compound [XIII] can be produced by reacting compound [VI] with a thiocarbonyl derivat ive such as N,N'-thiocarbonyldiimidazole or phenyl chlorothioformate in a suitable solvent such as anhydrous pyridine at 20°–70° C. for 2–10 hours.

Reduction of compound [XIII] can be carried out by the known method, for example using 4–5 equivalents of tributyltin hydride and a catalytic amount of azoisobutyronitrile in a hydrocarbon solvent such as benzene or toluene at 70°–110° C.

Deprotection of the resulting compound can be carried out by the known procedure, for example by treatment with tetrabutylammonium fluoride or a mineral acid such as hydrochloric acid and then with concentrated aqueous ammonia. In this procedure, the order of said treatment with tetrabutylammonium fluoride or a mineral acid such as hydrochloric acid and said treatment with concentrated aqueous ammonia may be reversed.

Process B (1) In the case of a purine base

The compound [Ie] of the present invention can also be produced, for example, by the reactions illustrated in the following schema.

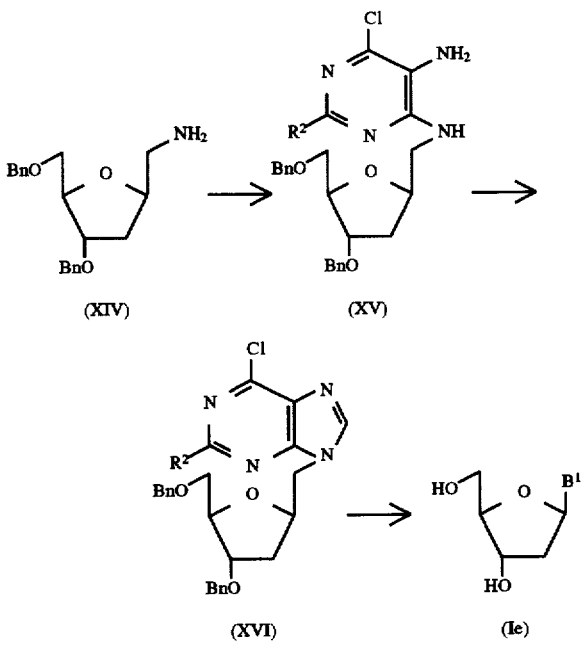

wherein $B^1$ has the same meaning as defined hereinbefore; $R^2$ represents hydrogen or amino; Bn represents benzyl.

Thus, compound [XVI] can be produced by reacting compound [XIV] with an 5-amino-4, 6-dichloropyrimidine compound to give a compound [XV] and cyclizing compound [XV]. Then, after substitution of a suitable substituent group (amino for an adenine base; hydroxy for a guanine base) for the chlorine atom of compound [XVI], catalytic reduction is carried out, whereby compound [Ie] can be produced.

The reaction of compound [XIV] with an 5-amino-4,6-dichloropyrimidine compound can be carried out in the presence of a base such as triethylamine, in a lower alcohol solvent, preferably in n-butanol, at 60°–130° C.

The cyclized compound [XVI] can be obtained by reacting compound [XV] with ethyl orthoformate in the presence of a mineral acid catalyst such as hydrochloric acid, at room temperature for 5–24 hours.

Compound [XVI] is reacted with ammonia in a hermetically sealed reaction tube in the conventional manner to substitute an amino group for the chlorine atom, whereby the compound whose nucleic acid base is adenine can be produced. Moreover, by subjecting compound [XVI] to acid or alkali hydrolysis in the conventional manner, a hydroxyl group is substituted for the chlorine atom, whereby the compound whose nucleic acid base is guanine can be produced.

Compound [Ie] can be produced by subjecting the resulting compound to catalytic reduction in the presence of a catalyst such as palladium chloride or 5% or 10% palladium-on-carbon, in a lower alcohol solvent such as methanol or ethanol at room temperature for 0.5–4 hours.

(2) In the case of a pyrimidine base

The compound [If] that is the compound [I] of the invention wherein X represents hydroxy and Y represents hydrogen and whose nucleic acid base is a pyrimidine base can be produced, for example, by the reactions illustrated in the following schema.

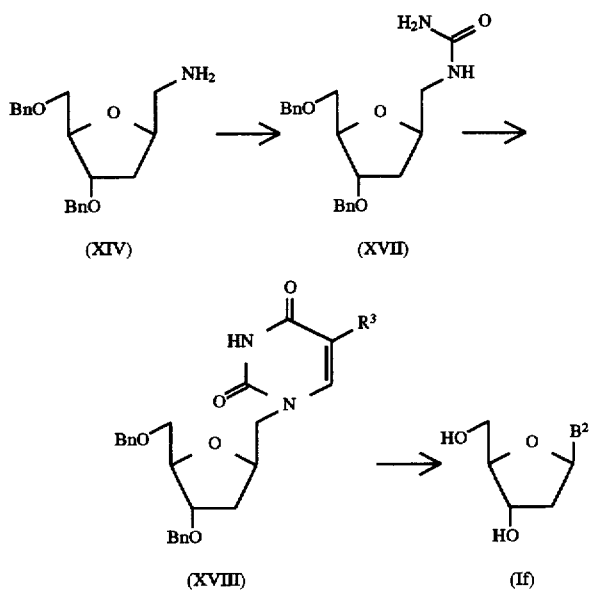

In the schema, B² represents uracil-1-ylmethyl or thymin-1-ylmethyl; R³ represents hydrogen or methyl; Bn represents benzyl.

Thus, compound [If] can be produced by reacting compound [XIV] with nitrourea to give compound [XVII], then cyclizing this compound to compound [XVIII], and subjecting this compound [XVIII] to catalytic reduction.

The reaction of compound [XIV] with nitrourea can be carried out by heating them together in a solvent mixture of water and a lower alcohol such as ethanol at 60°–110° C. for 2–10 hours and then stirring the reaction mixture at room temperature for 5–24 hours.

Compound [XVII] is reacted with a suitable reagent (2-methyl-3-methoxypropenoyl chloride or 2-methyl-3-ethoxypropenoyl chloride for thymine ring formation or 3-methoxypropenoyl chloride or 3-ethoxypropenoyl chloride for uracil ring formation) in the presence of a base such as pyridine in a solvent such as methylene chloride at room temperature for 5–24 hours and, then, reacted with a mixture of acetic acid and concentrated hydrochloric acid at room temperature overnight, whereby the cyclized compound [XVIII] can be obtained.

Catalytic reduction of compound [XVIII] can be carried out by treating compound [XVIII] in the presence of a catalyst such as palladium chloride or 5% or 10% palladium-on-carbon, in a lower alcohol solvent such as methanol or ethanol, at room temperature for 0.5–4 hours.

The compound [I] of the invention wherein B represents hypoxanthin-9-ylmethyl can be produced by reacting the corresponding compound [I] wherein B is adenin-9-ylmethyl with sodium nitrite in acetic acid/water at room temperature.

The compound of the invention wherein B is cytosin-1-ylmethyl can be produced from the compound [I] of the invention wherein B is uracil-1-ylmethyl by the method described in the literature (Carbohydrate Research, 31, 245–254, 1973) or any method analogous therewith.

Compound [III] which is used as the starting material for the production of compound [I] of the present invention can be produced by any of the methods disclosed in the above-mentioned literatures describing homonucleosides and the methods described in the reference examples presented hereinafter. Moreover, compound [XIV] can be produced by the method described in the reference examples.

Compound [III] of the invention wherein B is guanin-9-ylmethyl or thymin-1-ylmethyl is a novel compound not heretofore described in the literature and is useful as the starting material for the production of compound [I] of the present invention.

Having potent antiviral activity, the compound of the present invention is not only expected to act against influenza viruses, hepatitis A, B, and C viruses, labial and genital herpes viruses, herpes simplex 1 and 2 viruses in immunosuppressed cases, cytomegarovirus which causes serious pneumonia in immunosuppressed cases, varicella zoster virus which is a pathogenic agent of chickenpox and zona, AIDS virus, etc. but also expected to be a useful therapeutic agent for malignant tumors.

For administration of the compound of the invention as a medicine, it can be administered to animals inclusive of human being, either as it or in the form of a pharmaceutical composition containing, for example, 0.1–99.5%, preferably 0.5–90% of the compound in a pharmaceutically acceptable, nontoxic and inert carrier.

As the carrier, one or more formulation auxiliaries such as solid, semisolid and liquid diluents, fillers, and other auxiliary agents can be selectively employed. The pharmaceutical composition is preferably administered in a unit dosage form. The pharmaceutical composition of the present invention can be administered intravenously, orally, into the target tissue, locally (transdermal delivery) or rectally. Of course, the dosage form suited to each route of administration should be used. The oral route is particularly preferred.

The dosage as an antiviral or antimalignant-tumoral drug is preferably selected with reference to patient conditions such as age and body weight, route of administration, nature and severity of illness, and other factors. Usually, for adults, the daily dose of 50–600 mg/man, preferably 100–300 mg/man, in terms of the active ingredient compound of the invention is general.

Doses lower than the above range may be sufficient in some cases, while higher doses may be needed in other cases. Moreover, It is also possible to give twice or thrice daily by dividing the daily dose in to two or three.

BEST MODE OF CARRYING OUT THE INVENTION

The following reference and working examples are intended to describe the present invention in further detail.

Reference Example 1

1-Amino-2,5-anhydro-4,6-di-O-benzyl-1,3-dideoxy-D-allitol

Step 1 1-β-cyano-3,5-di-O-benzyl-2-deoxy-D-ribose

In 30 ml of methylene chloride was dissolved 1.3 g of 1-methoxy-3,5-di-O-benzyl-2-deoxy-D-ribose, and then 46.8 μl of a solution of 0.1 equivalent of boron trifluoride-ether complex solution was added under ice-cooling. Then, 3.12 ml of trimethylsilyl cyanide was further added and the mixture was stirred at room temperature for 3 hours. This reaction mixture was poured in a cold saturated aqueous solution of sodium hydrogen carbonate and the methylene chloride layer was washed with saturated aqueous sodium chloride solution, dried over anhydrous sodium sulfate, and filtered. The filtrate was concentrated and the residue was purified by silica gel column chromatography (ethyl acetate/ n-hexane=1/9) to provide 400 mg of the desirable compound and 450 mg of 1-α-cyano-3,5-di-O-benzyl-2-deoxy-D-ribose, each as yel low oily substance.

Step 2 1-Amino-2,5-anhydro-4,6-di-O-benzyl-1,3-dideoxy-D-allitol

In 30 ml of tetrahydrofuran (THF) was dissolved 4.4 g of 1-β-cyano-3, 5-di-O-benzyl-2-deoxy-D-ribose and then 1.78 g of borane-dimethyl sulfide complex salt was added in small portions under reflux. After 45 minutes of refluxing, the reaction mixture was ice-cooled and 54 ml of 2N-hydrochloric acid was added. The mixture was then stirred at 50° C. for 1.5 hours and thereafter at room temperature overnight. The reaction mixture was then neutralized with 1N-aqueous sodium hydroxide solution and extracted with ethyl acetate. The organic layer was washed with saturated aqueous sodium chloride solution, dried over anhydrous sodium sulfate, and filtered. The filtrate was concentrated to provide 4.4 g of the desirable compound as pale yellow oily substance.

Reference Example 2

2,5-Anhydro-1-deoxy-1-(thymin-1-yl)-D-allitol

Step 1 1-Ureido-2,5-anhydro-3,4-O-isopropylidene-1-deoxy-D-allitol

A mixture of 818 mg of 1-amino-2,5-anhydro-3,4-O-isopropylidene-1-deoxy-D-allitol and 465 mg of nitrourea was stirred in 3.5 ml of 50% ethanol/water at 90° C. for 5 hours. This reaction mixture was concentrated and the residue was purified by silica gel column chromatography (methylene chloride→7% methanol/methylene chloride) to provide 631 mg of the desirable compound as a colorless foamy substance.

Step 2 6-O-Acetyl-1-[N-(2-methyl-3-methoxypropenoyl)ureido]-2,5-anhydro-3,4-O-isopropylidene -1-deoxy-D-allitol In 1 ml of pyridine was dissolved 314 mg of 1-ureido-2, 5-anhydro-3,4-O-isoproopylidene-1-deoxy-D-allitol followed by addition of 1 ml of acetic anhydride, and the mixture was stirred at room temperature for 1 hour. This reaction mixture was concentrated and the residue was subjected to azeotropic dehydration with toluene 3 times and then dissolved in 8 ml of methylene chloride/pyridine (3/1), and 360 mg of 2-methyl-3-methoxypropenoyl chloride was added. This mixture was stirred at room temperature overnight. The reaction mixture was then poured in 5% aqueous monopotassium phosphate solution and extracted with ethyl acetate. The organic layer was washed serially with 5% aqueous monopotassium phosphate solution twice, saturated aqueous sodium hydrogen carbonate solution once, and water once, dried over anhydrous sodium sulfate, and filtered. The filtrate was concentrated and the residue was purified by TLC (5% methanol/methylene chloride) to provide 284 mg of the desirable compound as an oily substance.

Step 3 2, 5-Anhydro-1-deoxy-1-(thymin-1-yl)-D-allitol

In a mixture of 0.47 ml of acetic acid and 4.75 ml of concentrated hydrochloric acid, 258 mg of 6-O-acetyl-1-[N-(2-methyl-3-methoxypropenoyl)-ureido]-2,5-anhydro -3,4-O-isopropylidene-1-deoxy-D-allitol was added and stirred at room temperature overnight. This reaction mixture was concentrated and the residue was stirred in ethanol (4 ml)/water(8 ml)/0.6N-hydrochloric acid(4 ml) at 100° C. for 30 minutes. The reaction mixture was then concentrated and the residue was subjected to azeotropic dehydration with toluene 3 times and then stirred in concentrated aqueous ammonia(5 ml)/methanol (3.2 ml) overnight. This reaction mixture was concentrated and the residue was purified by ODS column chromatography (water→10% methanol/water) to provide 180 mg of the desirable compound as white powder.

UV: $\lambda_{max}$ (H$_2$O, ph=7) 271.2 nm

IR: cm$^{-1}$ (KBr) 3400, 1682, 1473.8, 1224.9, 1105.3, 1051.3

Reference Example 3

2,5-Anhydro-1-deoxy-1-(guanin-9-yl)-D-allitol

Step 1 1-Deoxy-1-(2,5-diamino-6-chloro-4-pyrimidinylamino)-2,5-anhydro-3,4-O-isopropylidene-D-allitol In a mixture of 2 ml of n-butanol and 3 ml of DMF, 340 mg of 1-amino-2,5-anhydro-3,4-O-isopropylidene-1-deoxy-D-allitol, 200 mg of 2,5-diamino-4,6-dichloropyrimidine and 384 μl of triethylamine were stirred together at 100° C. for 6.5 hours and then at room temperature overnight. This reaction mixture was concentrated and the residue was purified by silica gel column chromatography (methylene chloride→3% methanol/methylene chloride) to provide 110 mg of the desirable compound as brown oily substance.

Step 2 2,5-Anhydro-1-deoxy-1-(guanin-9-yl)-D-allitol

In a mixture of 1.1 ml ethyl orthoformate and 45 μl concentrated hydrochloric acid, 100 mg of 1-deoxy-1-(2,5-diamino-6-chloro-4-pyrimidinyl-amino)-2,5-anhydro -3,4-O-isopropylidene-D-allitol was stirred at room temperature overnight. This reaction mixture was concentrated to dryness and stirred in ethanol(3.2 ml)/water(6.4 ml)/0.6N-hydrochloric acid (3.2 ml) at 100° C. for 30 minutes. The reaction mixture was then neutralized with 20% sodium hydroxide. After addition of 520 mg of sodium hydroxide, the mixture was refluxed for 6.5 hours. This reaction mixture was neutralized with 6N-hydrochloric acid and the residue was purified by ODS column chromatography (water→10% methanol/water) to provide 34 mg of the desirable compound as white powder.

UV: $\lambda_{max}$ (H$_2$O, pH=7) 252.8 nm

EXAMPLE 1

2,5-Anhydro-1,3,4-trideoxy-1-(adenin-9-yl)-D-allitol

Step 1 2,5-Arthydro-3,4-didehydro-1,3,4-trideoxy-1-(adenin-9-yl)-D-allitol

In 0.5 ml of acetonitrile was dissolved 28 mg of 2,5-anhydro-1-deoxy-1-(adenin-9-yl)-D-allitol followed by addition of 65 μl of 2-acetoxyisobutyryl bromide at room temperature. After 1 hour, saturated aqueous sodium hydrogen carbonate solution was added and the mixture was partitioned between methylene chloride and water. The organic layer was dried over anhydrous sodium sulfate and concentrated to dryness to give a crude product. This product was dissolved in a mixture of 0.2 ml of methylene chloride and 0.8 ml of methanol followed by addition of 0.5 ml of a methanolic suspension of Zn (Cu) couple reagent (prepared in accordance with the method described in Org. Chem., 54, 4785–95 (1989)), and then the mixture was stirred at room temperature for 30 minutes. After the depletion of the starting material was confirmed by microsilica gel TLC (developping solvent: ethyl acetate/acetone=5/1), the reaction mixture was filtered through celite. The liltrate was concentrated to dryness and the residue was stirred in methanol (3.0 ml)/concentrated aqueous ammonia (10 ml) at room temperature overnight. The reaction mixture was then concentrated to dryness and the residue was purified by open reversed-phase ODS chromatography (gradient elution with 0% methanol/water→30% methanol/water) to provide 20 mg of the desirable compound as white powder. m.p. 225°–228° C. (decomp.)

UV: $\lambda_{max}$ (H$_2$O, pH=7) 261.4 nm

FAB-MS: 248 (M+H)$^+$

Step 2 2,5-Anhydro-1,3,4-trideoxy-1-(adenin-9-yl)-D-allitol

In 90% ethanol was dissolved 30 mg of 2,5-anhydro-3,4-didehydro-1,3,4-trideoxy-1-(adenin-9-yl) -D-allitol followed by addition of 20 mg of 1076 Pd-C, and then catalytic reduction was carried out at room temperature for 4 hours. After completion of the reaction, the reaction mixture was filtered through celite. The filtrate was concentrated to dryness and pulverized from acetone/ethanol to provide 29 mg of the desirable compound as white solid. m.p. 199°–201° C.

FAB-MS :250 (M+H)$^+$

UV: $\lambda_{max}$ (H$_2$O, pH=7) 261.2 nm

EXAMPLE 2

2, 5-Anhydro-1,3,4-trideoxy-1-(hypoxanthin-9-yl)-D-allitol

To a solution of 15 mg 2,5-anhydro-1,3,4-trideoxy-1-(adenin-9-yl)-D-allitol in 2N-acetic acid was added 1.2 ml of 2196 aqueous sodium nitrite and the mixture was allowed to stand at room temperature. This reaction mixture was purified by open ODS chromatography (gradient elution with 0% methanol/water→20% methanol/water) and pulverized from acetone/ethanol to provide 15.6 mg of the desirable compound as white solid. m.p. 220°–222° C.

FAB-MS: 251 (M+H)$^+$

UV: $\lambda_{max}$ (H$_2$O, pH=7) 250.2 nm

EXAMPLE 3

2,5-Anhydro-1,3,4-trideoxy-1-(thymin-1-yl)-D-allitol

Step 1 2,5-Anhydro-6-O-acetyl-3,4-didehydro-1,3,4-trideoxy-1-(thymin-1-yl)-D-allitol In 4.5 ml of acetonitrile was suspended 120 mg of the 2,5-anhydro-1-deoxy-1-(thymin-1-yl)-D-allitol obtained in Reference Example 2 followed by addition of 320 µl of 2-acetoxyisobutyryl bromide at room temperature. In about 2 minutes the reaction mixture became homogeneous. This reaction mixture was refluxed at 100° C. for 2 hours, after which it was cooled, cold saturated aqueous solution of sodium hydrogen carbonate was added into it, and partitioned between methylene chloride and water. The organic layer was dried over anhydrous sodium sulfate and concentrated to dryness to give a light yellow solid. This solid was dissolved in a mixture of 1.2 ml of methylene chloride and 4.8 ml of methanol followed by addition of about 2.0 ml of a suspension of Zn (Cu) couple reagent in methanol and then the mixture was stirred at room temperature for 40 minutes. This reaction mixture was filtered through celite and the liltrate was concentrated to dryness. To the residue was added 30 ml of concentrated aqueous ammonia/methanol (3/1) and the mixture was stirred at room temperature for 3 hours. After the reaction mixture was concentrated to dryness, 10 ml of acetic anhydride/pyridine (1/1) was added at room temperature and after 1 hour the mixture was concentrated to dryness. The residue was partitioned between methylene chloride and water and the organic layer was dried, concentrated to dryness, and purified by TLC (5% methanol/methylene chloride) to provide 95 mg of the desirable compound as white powder.

Step 2 2,5-Anhydro-1,3,4-trideoxy-1-(thymin-1-yl)-D-allitol

To 5 ml of a methanolic solution of 88 mg of 2,5-anhydro-6-O-acetyl-3,4-didehydro-1,3,4-trideoxy -1-(thymin-1-yl)-D-allitol was added 5 ml of concentrated aqueous ammonia and the mixture was stirred at room temperature overnight. This reaction mixture was concentrated to dryness followed by dissolution in 15 ml of 90% ethanol. To this solution was added 30 mg of 10% Pd-C and catalytic reduction was carried out at room temperature for 5 hours. After completion of the reaction, the catalyst was removed by filtration through filter paper and the filtrate was concentrated to dryness. The residue was purified by open ODS chromatography (elution gradient: 0% methanol/water→10% methanol/water) to provide 56 mg of the desirable compound as white powder. m.p. 133°–135° C.

EI-MS: 240 (M$^+$)

UV: $\lambda_{max}$ (H$_2$O, pH=7) 271.4 mn

EXAMPLE 4

2,5-Anhydro-1-deoxy-1-(adenin-9-yl)-D-sorbitol

Step 1 2,5-Anhydro-1-deoxy-1- (N-benzoyladenin-9-yl)-D-allitol 2,5-Anhydro-1-deoxy-1- (adenin-9-yl) -D-allitol (916 mg) was subjected to azeotropic dehydration with anhydrous pyridine and then suspended in 15 ml of anhydrous pyridine. To the suspension was added 2.75 g of benzoyl chloride dropwise under ice-cooling. After the mixture was reacted at room temperature for 2 hours, it was poured into a mixture of 114 g of ice, 9 g of sodium hydrogen carbonate and 100 ml of chloroform and extracted with chloroform. The chloroform layer was concentrated and ethanol/pyridine was added to the residue. Then, 13 ml of 2N-sodium hydroxide solution and 13 ml of ethanol were added under water-cooling and the reaction was carried out at room temperature for 30 minutes. This reaction mixture was neutralized by adding about 13 ml of 2N-hydrochloric acid under cooling and concentrated under reduced pressure. The residue was washed with ether and the aqueous layer was concentrated under reduced pressure. The residue was purified by reversed phase column chromatography (methanol/water) to provide 1.28 g of the desirable compound. m.p. 85°–90° C.

FAB-MS: 386 (M+H)$^+$

UV: $\lambda_{max}$ (H$_2$O, pH=7) 282.0 nm

Step 2 2,5-Anhydro-1-deoxy-1-(N-benzoyladenin-9-yl) -4,6-O-(tretraisopropyldisiloxane-1,3-diyl) -D-alliotol To a solution of 160 mg of 2,5-anhydro-1-deoxy-1-(N-benzoyladenin-9-yl)-D-allitol in DMF(1 ml) were added 113 mg of imidazole and 153 mg of 1,1,3,3-tetraisopropyl-1,3-dichlorodisiloxane and the mixture was allowed to stand at room temperature for 3 hours. After completion of the reaction, the reaction mixture was partitioned between methylene chloride and water, and the organic layer was washed with saturated sodium hydrogen carbonate solution and water. The organic layer was dried, concentrated to dryness, and purified by TIC (5% methanol/methylene chloride) to provide 182 mg of the desirable compound as white powder.

Step 3 2,5-Anhydro-1-deoxy-1-(N-benzoyladenin-9-yl)-4,6-O-(tetraisooproopyldisiloxane-1,3-diyl) -3-O-trifluoromethanesulfonyl-D-allitol In 3 ml of pyridine/methylene chloride (1/1) was dissolved 113 mg of 2,5-anhydro-1-deoxy-1-(N- benzoyladenin-9-yl)-4,6-O-(tetraisopropyl disiloxane-1,3-diyl)-D-allitol. After the solution was cooled to 0° C., 210 mg of trifluoro-methanesulfonic anhydride was added and the mixture was stirred for 1 hour. After completion of the reaction, the mixture was partitioned between methylene chloride and cold water and the methylene chloride layer was dried, concentrated to dryness, and purified by TLC (5% methanol/methylene chloride and then 2% methanol/methylene chloride) to provide 117 mg of the desirable compound as white powder. m.p. 107°–109° C.

FAB-MS: 760 (M+H)$^+$

UV: $\lambda_{max}$ (H$_2$O, pH=7) 280.8 nm

Step 4 2,5-Anhydro-1-deoxy-1-(N-benzoyladenin-9-yl)-4,6-O-(tetraisopropyldisiloxane-1,3-diyl) -3-O -acetyl-D-sorbitol To a solution of 45 mg of 2,5-anhydro-1-deoxy-1-(N-benzoyladenin-9-yl)-4,6-O-(tetraisopropyldisiloxane -1,3-diyl) -3-O-trifluoronaethanesulfonyl-D-allitol in DMF (0.9ml) was added 39 mg of anhydrous lithium acetate and the mixture was stirred at room temperature overnight. After completion of the reaction, the reaction mixture was concentrated to dryness and purified by TLC (4% naethanol/methylene chloride) to provide 32 mg of the desirable compound as white solid.

FAB-MS: 670 (M+H)$^+$

UV: $\lambda_{max}$ (H$_2$O, pH=7) 280.5 nm

Step 5 2,5-Anhydro-1-deoxy-1-(adenin-9-yl)-D-sorbitol

To a solution of 32 mg 2,5-anhydro-1-deoxy-1-(N-benzoyladenin-9-yl)-4,6-O-(tetraisopropyldisiloxane -1,3-diyl)-3-O-acetyl-D-sorbitol in THF(0.5ml) was added 70 µl of a solution of tetrabutylammonium fluoride in THF at room temperature. After 5 minutes, 0.1 ml of 50% pyridine/water was added and the reaction mixture was concentrated to dryness. To the residue were added 3.0 ml of methanol and 3.0 ml of concentrated aqueous ammonia and then the mixture was allowed to stand at room temperature overnight. This reaction mixture was concentrated to dryness and purified by open ODS chronaatography (elution gradient: 0% methanol/water→10% methanol/water) to provide 18.4 mg of the desirable compound as white powder. m.p. 260°–263° C.

EI-MS: 281 (M$^+$)

UV: $\lambda_{max}$ (H$_2$O, pH=7) 261.2 nm

EXAMPLE 5

2, 5-Anhydro-1-deoxy-1-(uracil-1-yl)-D-sorbitol

Step 1 2,5-Anhydro-1-deoxy-1-(uracil-1-yl)-4,6-O-(tetraisopropyldisiloxane-1,3-diyl)-D-allitol Using 516 mg of 2,5-anhydro-1-deoxy-1-(uracil-1-yl)-D-allitol, the same procedure as Example 4, Step 2 was carried out to provide 760 mg of the desirable compound as white solid.

FAB-MS: 501 (M+H)$^+$

Step 2 2,5-Anhydro-1-deoxy-(uracil-1'-yl)-4,6-O-(tetraisopropyldisiloxane-1,3-diyl)-2',3-anhydro -D-sorbitol In 3.6 ml of pyridine/water (1/1) was dissolved 150 mg of 2,5-anhydro-1-deoxy-1-(uracil-1-yl) -4,6-O-(tetraisopropyl-disiloxane-1,3-diyl)-D-allitol, and after the solution was cooled to 0° C., and then a solution of 169 mg trifluoro-methanesulfonic anhydride in methylene chloride (0.5ml) was added. After 1 hour, the temperature was allowed to rise gradually to room temperature. After one and half more hours, the reaction mixture was partitioned between methylene chloride and saturated aqueous sodium hydrogen carbonate solution, and water in turn. The organic layer was dried, concentrated to dryness followed by purification by TLC (5% methanol/methylene chloride) to provide 84 mg of the desirable compound as light brown solid.

FAB-MS: 483 (M+H)$^+$

Step 3 2,5-Anhydro-1-deoxy-1-(uracil-1-yl)-D-sorbitol

To a solution of 80 mg of 2,5-anhydro-1-deoxy-1-(uracil-1'-yl)-4,6-O-(tetraisopropyldisiloxane-1,3-diyl) -2',3-anhydro-D-sorbitol in methanol (4.0ml) was added 4.0 ml of 0.6N-hydrochloric acid and then the mixture was stirred at room temperature overnight. After completion of the reaction, the reaction mixture was concentrated to dryness followed by purification by open reversed phase column chromatography (water) to provide 40 mg of the desirable compound as white solid. m.p. 183°–184° C.

FAB-MS: 259 (M+H)$^+$

UV: $\lambda_{max}$ (H$_2$O, pH=7) 265.6 nm

EXAMPLE 6

2, 5-Anhydro-1-deoxy-1-(cytosin-1-yl)-D-sorbitol

Step 1 3,4,6-Tri-O-acetyl-2,5-anhydro-1-deoxy-1-(4-thiouracil-1-yl)-D-sorbitol

The 2,5-anhydro-1-deoxy-(uracil-1-yl)-D-sorbitol (110 mg) obtained in Example 5 was reacted with 2 ml of acetic anhydride and 2 ml of pyridine at room temperature for 1.5 hours and the reaction mixture was then concentrated to dryness. The residue was partitioned between methylene chloride and water and the organic layer was dried. The solvent was evaporated off and the resulting crude product was subjected to azeotropic dehydration with toluene twice and with pyridine twice and dissolved in 8 ml of pyridine. Then, 473 mg of phosphorus pentasulfide was added thereto and the mixture was refluxed for 2 hours. The reaction mixture was then cooled to room temperature and 0.3 ml of water was added. The mixture was stirred at room temperature for 5 minutes. After the most solvent of the reaction mixture was evaporated off, the residue was partitioned methylene chloride and cold hydrochloric acid, cold saturated aqueous sodium hydrogen carbonate solution, and water in turn. The organic layer was dried and concentrated to dryness followed by purification by TIC (3.07% methanol/methylene chloride) to provide 135 mg of the desirable compound as yellow solid. m.p. 100°–105° C.

FAB-MS: 401 (M+H)$^+$

UV: $\lambda_{max}$ (H$_2$O, pH=7) 332.6 nm

Step 2 2,5-Anhydro-1-deoxy-1-(cytosin-1-yl)-D-sorbitol

In 30 ml of saturated amonia-methanol was dissolved 120 mg of 3,4,6-tri-O-acetyl-2,5-anhydro-1-deoxy-1-(4-thiouracil-1-yl)-D-sorbitol and the reaction was conducted in a hermetically sealed tube at 100° C. overnight. After completion of the reaction, the reaction mixture was concentrated to dryness followed by purification by open reversed phase column chromatography to provide 60 mg of the desirable compound as white solid. m.p. 230°–232° C.

FAB-MS: 258 (M+H)$^+$

UV: $\lambda_{max}$ (H$_2$O, pH=7) 273.0 nm

EXAMPLE 7

2,5-Anhydro-1,3-dideoxy-1-(adenin-9-yl)-D-allitol

Step 1 2,5-Anhydro-1-deoxy-1-(N-benzoyladenin-9-yl)-4,6-O-(tetraisopropyldisiloxane-1,3-diyl) -3-O-(imidazol-1-ylthiocarbonyl)-D-allitol The 2, 5-anhydro-1-deoxy-1-(N-benzoyladenin-9-yl)-4,6-O-(tetraisopropyldisiloxane-1,3-diyl) -D-allitol (148 mg)

obtained in Example 4, Step 2 was subjected to azeotropic dehydration with pyridine twice and dissolved in 2 ml of anhydrous pyridine. Then, 49 mg of N, N'-thiocarbonyldiimidazole was added and the reaction mixture was heated at 50° C. for 5 hours. After completion of the reaction, the reaction mixture was concentrated to dryness and purified by TLC to provide 150.4 mg of the desirable compound.

Step 2 2,5-Anhydro-1,3-dideoxy-1-(N-benzoyladenin-9-yl)-4,6-O-(tetraisopropyldisiloxane-1,3-diyl) -D-allitol A solution of 135 ms 2,5-anhydro-1-deoxy-1-(N-benzoyladenin-9-yl)-4,6-O-(tetraisopropyldisiloxane -1,3-diyl)-3-O-(imidazol-1-ylthiocarbonyl)-D-allitol in toluene (3ml) was refluxed and then a solution of 225 mg of tributyltin hydride and 22 mg of azoisobutyronitrile in toluene(2ml) was added dropwise over 5 minutes. After the mixture was further refluxed for 1.5 hours, it was cooled to room temperature and concentrated to dryness. The residue was purified by TLC to provide 67 mg of the desirable compound.

Step 3 2,5-Anhydro-1,3-dideoxy-1-(N-benzoyladenin-9-yl)-D-allitol

To a solution of 65 mg of 2,5-anhydro-1,3-dideoxy-1-(N-benzoyladenin-9-yl)-4,6-O-(tetraisopropyldisiloxane-1,3-diyl)-D-allitol in THF (0.3ml) was added 0.32 ml of tetrabutylammonium fluoride and the mixture was allowed to stand at room temperature for 10 minutes. After completion of the reaction, the reaction mixture was adjusted to pH 4.0 with diluted hydrochloric acid and concentrated to dryness. The residue was purified by open ODS chromatography (elution gradient: 0% methanol/water→45% methanol/water) to provide 30 mg of the desirable compound as white solid.

Step 4 2,5-Anhydro-1,3-dideoxy-1-(adenin-9-yl)-D-allitol

To 10 mg of 2,5 -anhydro- 1,3 -dideoxy-1-(N-benzoyladenin-9-yl)-D-allitol were added 1 ml of methanol and 0.5 ml of concentrated aqueous ammonia and then the mixture was allowed to stand at room temperature overnight. The reaction mixture was then concentrated to dryness and the residue was tritulated with ether to provide 6.0 mg of the desirable compound as white solid. m.p. 227°–230° C. Elemental analysis ($C_{11}H_{15}N_5O_3$)

Calcd. (%): C, 49.81; H, 5.70; N, 26.40

Found (%): C, 49.58; H, 5.54; N, 26.18

UV: $\lambda_{max}$ (MeOH, pH=7) 260.6 nm

EXAMPLE 8

An alternative process for producing 2, 5-anhydro-1,3-dideoxy-1-(adenin-9-yl)-D-allitol Step 1 1-(5-Amino-6-chloropyrimidin-4-yl-amino)-2,5-anhydro-4,6-di-O-benzyl-1,3-dideoxy -D-allitol In 48 ml of n-butanol were dissolved 2.5 g of 1-amino-2,5-anhydro-4,6-di-O-benzyl-1,3-dideoxy-D-allitol obtained in Reference Example 1, 1.8 g of 5-amino-4,6-dichloropyrimidine, and 1.65 ml of triethylamine and then the mixture was stirred at 110° C. for 6 hours. This reaction mixture was concentrated and the residue was purified by silica gel column chromatography (chloroform→1% methanol/chloroform) to provide 2.35 g of the desirable compound as brown oily substance.

Step 2 2,5-Arthydro-1-(6-chloropurin-9-yl )-4, 6-di-O-benzyl-1,3-dideoxy-D-allitol In 18 ml of ethyl orthoformate was dissolved 2.33 g of 1-(5-amino-6-chloropyrimidin-4-yl-amino) -2,5-anhydro-4,6-di-O-benzyl-D-allitol followed by addition of 722 µl of concentrated hydrochloric acid and the mixture was stirred at room temperature overnight. The reaction mixture was then concentrated and the residue was purified by silica gel column chromatography (chloroform→1% methanol/chloroform) to provide 1.89 g of the desirable compound as pale yellow crystals. m.p. 126°–129° C.

Step 3 2,5-Anhydro-1-(adenin-9-yl)-4,6-di-O-benzyl-1,3-dideoxy-D-allitol 2,5-Arthydro-1-(6-chloropurin-9-yl)-4,6-di-O-benzyl-1,3-dideoxy-D-allitol (1.8 g) was heated in 120 ml of saturated ammonia/methanol at 100° C. overnight. The reaction mixture was then concentrated and the residue was purified by silica gel column chromatography (1% methanol/chloroform→1.5% methanol/chloroform) to provide 1.42 g of the desirable compound as pale-yellow crystal s. m.p. 124°–127° C.

Step 4 2,5-Anhydro-1,3-dideoxy-1-(adenin-9yl)-D-allitol

In 50 ml of methanol was suspended 1 g of palladium chloride and the suspension was stirred in a hydrogen gas stream at atmospheric temperature and pressure for 45 minutes. Then, a solution of 1.2 g of 2,5-anhydro-1-(adenin-9-yl)-4,6-di-O-benzyl-1,3-dideoxy-D-allitol in methanol (50ml) was added and the mixture was further stirred in a hydrogen gas stream at atmospheric pressure and room temperature for 2 hours. The reaction mixture was then filtered and the filtrate was concentrated. The residue was neutralized with saturated sodium hydrogen carbonate solution followed by purification by ODS column chromatography (0% methanol/water→7% methanol/water) to provide 620 mg of the desirable compound as white powder. The physical constants of this compound were in complete agreement with those of the compound obtained in Example 7.

EXAMPLE 9

2,5-Anhydro-1,3-dideoxy-1-(thymin-1-yl)-D-allitol

Step 1 1-Ureido-2,5-anhydro-4,6-di-O-benzyl-1,3-dideoxy-D-allitol

1-Amino-2,5-arthydro-4,6-di-O-benzyl-1,3-dideoxy-D-allitol (2.4 g) obtained in Reference Example 1 and nitrourea (847 mg) were stirred together in 14 ml of 50% ethanol/water at 90° C. for 7 hours and further at room temperature overnight. This reaction mixture was concentrated and the residue was purified by silica gel column chromatography (chloroform→1% methanol/chloroform→2% methanol/chloroform) to provide 2.3 g of the desirable compound as pale-yellow oily substance.

Step 2 1-[N-(2-methyl-3-methoxypropenoyl)ureido]-2,5-anhydro-4,6-di-O-benzyl-1,3-dideoxy-D-allitol In 32.2 ml of methylene chloride was dissolved 2.3 g of 1-ureido-2,5-anhydro-4,6-di-O-benzyl-1,3-dideoxy-D-allitol followed by addit ion of 9.2 ml of pyridine. Then, 1.67 g of 2-methyl-3-methoxypropenoyl chloride was added and the mixture was stirred at room temperature overnight. This reaction mixture was poured in 5% aqueous solution of monopotassium phosphate followed by extraction with ethyl acetate. The organic layer was washed with 5% aqueous monopotassium phosphate solut ion thrice, saturated aqueous sodium hydrogen carbonate solution once, and saturated aqueous sodium chloride solution once in turn, dried over anhydrous sodium sulfate, and filtered. The filtrate was concentrated and the residue was purified by silica gel column chromatography (chloroform→1% methanol/chloroform) to provide 2.3 g of the desirable compound as pale-yellow oily substance.

17

Step 3  2,5-Anhydro-4,6-di-O-benzyl-1,3-dideoxy-1-(thymin-1-yl)-D-allitol

1-[N-(2-methyl-3-methoxypropenoyl)ureido]-2,5-anhydro-4,6-di -O-benzyl-1,3-dideoxy-D-allitol (2.3 g) was stirred in acetic acid (36 ml)—concentrated hydrochloric acid (3.6 ml) at room temperature overnight. This reaction mixture was concentrated and the residue was purified by silica gel column chromatography (chloroform→1% methanol/chloroform) to provide 1.6 g of the desirable compound as pale-yellow oily substance.

Step 4  2,5-Anhydro-1,3-dideoxy-1-(thymin-1-yl)-D-allitol

In a mixture of 150 ml of methanol and 1 ml of acetic acid were suspended 1.6 g of 2,5-anhydro-4,6-di-O-benzyl-1,3-dideoxy-1-(thymin-1-yl)-D-allitol and 1 g of 10% Pd-C and then the suspension was stirred in a hydrogen gas stream at atmospheric pressure and room temperature overnight. The reaction mixture was then filtered. The liltrate was concentrated and the residue was purified by DS column chromatography (0% methanol/water→3% methanol/water) to provide 850 mg of the desirable compound as white powder. m.p. 111°–114° C.

Elemental analysis ($C_{11}H_{16}N_2O_5 \cdot H_2O$)
Calcd. (%): C, 48.17; H, 6.61; N, 10.21
Found (%): C, 47.90; H, 6.43; N, 10.22
UV: $\lambda_{max}$ (MeOH, pH=7) 270.2 nm.

18

We claim:

1. A nucleoside derivative of the following general formula [I]:

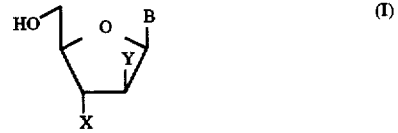

(I)

wherein B represents adenin-9-ylmethyl, guanin-9-ylmethyl, hypoxanthin-9-ylmethyl, thymin-1-ylmethyl, uracil-1-ylmethyl, or cytosin-1-ylmethyl; X and Y may be the same or different and each represents hydrogen or hydroxy, exclusive of the case in which X is hydrogen and Y is hydroxy.

2. A nucleoside derivative of the following general formula [IIIc]:

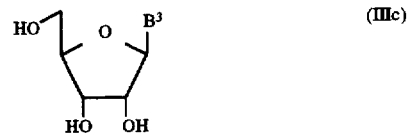

(IIIc)

whrein $B^3$ represents guanin-9-ylmethyl or thymin-1-ylmethyl.

* * * * *